(12) United States Patent
Eyal et al.

(10) Patent No.: US 7,019,170 B2
(45) Date of Patent: Mar. 28, 2006

(54) PROCESS FOR THE RECOVERY OF LACTIC ACID BY CONTACTING AQUEOUS SOLUTIONS CONTAINING THE SAME WITH A BASIC ORGANIC EXTRACTANT

(75) Inventors: Aharon Meir Eyal, Jerusalem (IL); Patrick R. Gruber, Blaine, MN (US); Rod R. Fisher, Eden Prairie, MN (US); Jeffrey J. Kolstad, Wayzata, MN (US)

(73) Assignee: Cargill Incorporated, Wayzata, MN (US)

( * ) Notice: Subject to any disclaimer, the term of this patent is extended or adjusted under 35 U.S.C. 154(b) by 0 days.

(21) Appl. No.: 09/284,160

(22) PCT Filed: Oct. 2, 1997

(86) PCT No.: PCT/US97/15844

§ 371 (c)(1),
(2), (4) Date: Oct. 25, 1999

(87) PCT Pub. No.: WO98/15517

PCT Pub. Date: Apr. 16, 1998

(65) Prior Publication Data

US 2003/0187300 A1    Oct. 2, 2003

(30) Foreign Application Priority Data

Oct. 9, 1996  (IL) ..................... 119387

(51) Int. Cl.
*C07C 59/08* (2006.01)
*C07C 51/42* (2006.01)

(52) U.S. Cl. ............... 562/589; 562/580; 562/593; 562/485

(58) Field of Classification Search ............... 562/580, 562/593, 485, 589
See application file for complete search history.

(56) References Cited

U.S. PATENT DOCUMENTS

| | | | | |
|---|---|---|---|---|
| 4,282,385 A | * | 8/1981 | Metz et al. | 562/589 |
| 4,444,881 A | * | 4/1984 | Urbas | 435/139 |
| 4,882,277 A | | 11/1989 | Czytko et al. | 435/136 |
| 5,132,456 A | | 7/1992 | King et al. | 562/593 |
| 5,210,296 A | * | 5/1993 | Cockrem et al. | 562/589 |
| 5,252,473 A | * | 10/1993 | Walkup et al. | 435/135 |
| 5,453,365 A | * | 9/1995 | Sterzel et al. | 435/135 |
| 5,510,526 A | * | 4/1996 | Baniel et al. | 562/580 |
| 5,766,439 A | * | 6/1998 | Eyal et al. | 204/524 |

FOREIGN PATENT DOCUMENTS

WO    9525081    9/1995

* cited by examiner

*Primary Examiner*—Cecilia J. Tsang
*Assistant Examiner*—Taylor Victor Oh
(74) *Attorney, Agent, or Firm*—Ladas & Parry

(57) ABSTRACT

The invention provides a process for the recovery of lactic acid and products thereof from an aqueous solution containing free lactic acid and at least one lactate salt at a total concentration of at least 5%, the process comprising the steps of: extracting at least 70% of the free lactic acid from the aqueous solution by contacting the solution with a basic extractant, to form a lactic acid-containing extract and a lactic acid-depleted, lactate salt-containing aqueous solution; separating the lactic acid-containing extract from the depleted aqueous solution; and stripping the extracted lactic acid from the extract by methods known per se, to form a solution of lactic acid and a stripped extractant.

20 Claims, No Drawings

PROCESS FOR THE RECOVERY OF LACTIC ACID BY CONTACTING AQUEOUS SOLUTIONS CONTAINING THE SAME WITH A BASIC ORGANIC EXTRACTANT

The present invention relates to a process for the recovery of lactic acid. More particularly, the present invention relates to a process for the recovery of lactic acid and products thereof from an aqueous solution containing free lactic acid and at least one lactate salt.

Lactic acid has long been used as a food additive and in various chemical and pharmaceutical applications. More recently, lactic acid has been used in the making of biodegradable polylactic acid polymers as a replacement for present plastic materials, as well as for various new uses where biodegradability is needed or desired. Accordingly, there is an ever-increasing demand for lactic acid. The present invention aims at meeting this demand by providing an efficient and environmentally friendly process for producing lactic acid which avoids the consumption of bases and acids and substantially reduces, if not eliminates, the formation of waste or byproduct salts.

The production of lactic acid is commonly carried out by fermentation of a strain of the bacterial genus *Lactobacillus*, and, for example, more particularly by the species *Lactobacillus delbrueckii* or *Lactobacillus acidophilus*. In general, the production of lactic acid by fermentation in a fermentation broth is well-known in the art. The fermentation substrate consists of carbohydrates together with suitable mineral and proteinaceous nutrients. Because the lactic acid-producing microorganisms are inhibited in a strongly acidic environment, lactic acid fermentation is usually conducted at about neutral pH and a neutralizing agent is added for pH adjustment. As the pKa of lactic acid is 3.86, at the pH of fermentation, practically only lactate salts exist. Thus, recovery of lactic acid in an acid form from the fermentation liquor requires chemical conversion. Several processes were developed for such conversion.

In some of the processes, the conversion liberates lactic acid in solution, e.g., by displacement with a strong acid. Thus, when calcium bases are used as the neutralizing agents in the fermentation, calcium lactate is formed. Reacting the calcium lactate-containing fermentation liquor with sulfuric acid results in precipitation of gypsum and liberation of lactic acid in the solution.

Nakanishi and Tsuda, in JP 46130176, consider production of 1-butyl lactate by extraction of an acidified crude fermentation broth with 1-butanol, followed by esterification of the extract phase. BASF (EP-0 159 585) considers a similar process with isobutanol, to form isobutyl lactate. The process of WO 93/00440, assigned to DuPont, comprises the steps of: (1) simultaneously mixing a strong acid, an alcohol, and a concentrated fermentation broth which contains mainly basic salts of lactic acid, which react to form a crystal precipitate comprising basic salts of the strong acid and an impure lactate ester of the alcohol; (2) removing water from the mixture as a water/alcohol azeotrop, which can be accomplished either sequentially or substantially simultaneously with step (1); (3) removing the crystal precipitate from the mixture; and (4) distilling the impure lactate ester to remove impurities and recovering the high purity ester.

Alternatively to purifying the lactic acid, which is liberated by displacement with a strong acid through esterification and distillation of the ester, one could purify it by extraction. The extractant could be a relatively weak one, and would allow the recovery of the extracted HLa at a high concentration by back-extraction. The known, and food-approved, weak extractants to be considered are amine-based or solvating extractants. One may consider esters, ethers, ketones, aldehydes, etc., but alkanols seem to be preferable.

Out of these two groups of weak extractants, the amine-based ones are more attractive, but they would not work in a simple process wherein the stronger than lactic displacing acid is added to the lactate salt-containing solution and the liberated HLa is directly extracted by contact with the extractant. The amine-based extractant prefers the stronger acid in a mixture, and would therefore reverse the reaction, removing the added acid.

Liquid-liquid extraction (LLE) proved to be an efficient way for recovering acidic fermentation products from fermentation liquors. Thus, a large fraction of the world's citric acid production uses an LLE process which recovers the acid from the broth by extraction with an extractant composed of a water-immiscible amine in a diluent. This extractant combines high recovery yields and high selectivity, resulting in a pure product and reversibility.

Baniel and co-inventors (U.S. Pat. No. 4,275,234) have found that the extracted acid can be recovered from the acid-containing extract by back-extraction with water. They have also found that, if the back-extraction is conducted at a temperature higher than that of the extraction, the concentration of the acid in the back-extract (the aqueous product of the back-extraction) could be significantly higher than that in the broth. Thus, in addition to the recovery at high yield and purity, extraction by an amine-based extractant provides for concentration of the recovered product and thereby for saving in energy consumption. An amine-based extractant similar to the one used in the citric acid process would be suitable for extraction of free lactic acid.

Acidulating neutral fermentation liquors by the addition of acids usually results in the formation of by-product salts, such as the gypsum in the example used above. Reagents are consumed and disposal of undesired by-products is required. Efforts have recently been made to recover lactic acid from fermentation liquors without the formation of by-product salts; such processes will be referred to herein as "salt-splitting processes."

In some recently published patents, LLE is applied for salt-splitting. Thus, in U.S. Pat. No. 5,132,456 (King), a strongly basic extractant extracts part of the lactic acid from the neutral solution, which results in a lactic acid-loaded extractant and a basic solution. This basic solution, which still contains most of the lactic acid values, could be recycled as a neutralizing medium to the fermentation. In U.S. Pat. No. 5,510,526 (Baniel), the extraction of the acid is conducted under $CO_2$ pressure so that a bicarbonate is formed. The latter can be used as a neutralizing agent in the fermentation. In order to limit the $CO_2$ pressure to an economic one and still achieve high yields, the extractant used should be quite strong.

Recently, new strains have been developed for lactic acid fermentation which can operate at slightly acidic conditions. It is expected that the fermentation pH will be further lowered on future development, probably at the cost of lowering the overall concentration in the solution. As long as the pH of the broth is >5, practically all of the product is still in the salt form. However, at a lower pH, a fraction of the lactic acid in the broth is not neutralized. Thus, at pH of 4.8 and 3.8, about 10% and about 50%, respectively, could be considered as being in free acid form.

It would not be expected that free lactic acid could be extracted efficiently from the lactate salt-containing broth by an amine-based extractant, due to the buffering effect of the salt. Amines extract acids through ion-pair formation and should therefore be positively charged. In the case of primary, secondary and tertiary amines (quaternary ones are not suitable for reversible extraction), the formation of the required positive charge is by binding protons (protonation) from the aqueous solution. Extraction efficiency is therefore determined by the availability of protons in the aqueous solution. Thus, extraction of the free lactic acid is strongly dependent on the concentration of the lactate salts in the solution:

$$[H]=Ka[HLa]/[La]$$

where [H], [HLa] and [La] denote the concentration of protons, undissociated lactic acid and lactate ions, respectively, and Ka is the dissociation constant of lactic acid. A significant lactate salt to free lactic acid ratio, or low free acid to salt ratio, substantially decreases the ratio [HLa]/[La] and thereby decreases the availability of protons in the aqueous solution and the protonation of the amine. Therefore, the efficiency of extraction of the free lactic acid is expected to be low. It would be even lower, if the extractant already contains lactic acid from a previous stage.

Recovery of the free lactic acid from the fermentation liquor by LLE, if feasible, would still leave lactate values, i.e., lactic acid and lactate salts, in the aqueous solution. Recycling of those values back to the fermentation is feasible, but quite problematic and costly, for several reasons: (a) since a complete recycle would build up impurities in the system, a bleed would be required, and treatment of the bleed stream would be needed to avoid significant losses; (b) a separate operation may be needed for the removal of traces of extractant from the recycled stream; (c) there would probably be a need to sterilize the recycle stream; and (d) water distillation from the recycled stream may be needed to maintain the water balance.

Alternatively, one can operate one of the salt-splitting processes for the recovery of lactic acid from the salts. If LLE processes are chosen, an extract loaded with lactic acid would be formed. Back-extraction of the lactic acid from this extract, as well as from the extract formed on the extraction of the free lactic acid, would be required. The lactic acid concentration in both extracts is expected to be low, due to the low activity of the lactic acid in the source from which it is extracted. That is particularly true for the salt-splitting process. The concentration of the lactic acid in the back-extract is therefore expected to be low.

U.S. Pat. No. 5,132,456 suggests a way to recover extracted carboxylic acid from extracts formed on LLE-based salt-splitting. It comprises leaching or back-extraction with an aqueous solution of ammonia or low molecular weight alkyl amine, especially trimethyl amine (TMA). The resultant aqueous ammonium or alkylammonium carboxylate solution can be concentrated, if necessary, and the carboxylate can be decomposed thermally to yield the product carboxylic acid and ammonia or amine, which can be condensed and recycled. This process is costly and complex, and is particularly problematic for recovery of extracted lactic acid, as stated in said patent:

"For lactic acid, the decomposition is incomplete, being stopped by the formation of a viscous, almost glassy mass containing polymerized lactic acid along with substantial TMA and water. There are, however, effective ways of driving the decomposition to completion for lactic acid, such as diluting the viscous mass with an appropriate solvent (e.g., methyl isobutyl ketone) and continuing the heating and decomposition process."

With the above state of the art in mind, it has now been surprisingly found that a basic extractant is capable of extracting most of the free acid from a fermentation liquor, even if the free lactic acid to lactate salt ratio in it is lower than 1:3. Furthermore, high yield of extraction was found, even with an extractant that comprises lactic acid from a previous step.

Thus, according to the present invention, there is provided a process for the recovery of lactic acid and products thereof from an aqueous solution containing free lactic acid and at least one lactate salt at a total concentration of at least 5%, said process comprising the steps of: (a) extracting at least 70% of the free lactic acid from said aqueous solution by contacting said solution with a water-immiscible basic amine extractant, to form a lactic acid-containing amine extract and a lactic acid-depleted, lactate salt-containing aqueous raffinate solution; (b) separating said lactic acid-containing amine extract from said depleted aqueous raffinate solution; and (c) stripping the extracted lactic acid from said extract by methods known per se, to form a solution of lactic acid and a stripped extractant.

In a preferred embodiment of the present invention said process further comprises the step of (d) recovering lactic acid and products thereof from said lactate salt in said lactic acid-depleted aqueous solution by methods known per se.

Preferably said process is carried out on an aqueous solution containing free lactic acid and at least one lactate salt wherein the ratio between said free lactic acid and said lactate salt is between 1:9 and 5:1, and most preferably on an aqueous solution wherein the ratio between said free lactic acid and said Lactate salt is between 1:9 and 3:1.

In an especially preferred embodiment of the present invention said basic extractant comprises a portion of lactic acid, preferably at least 3% lactic acid extracted in a previous step, and said solution is contacted with said extractant to form an extract comprising lactic acid in an amount greater than said portion and a lactic acid-depleted, lactate salt-containing aqueous solution. In especially preferred embodiments of the present invention the basic extractant used in step (a) comprises at least 5% lactic acid extracted in previous step.

Preferably said basic extractant in step (a) has a basicity corresponding to a pKa lower than 7 and in especially preferred embodiments of the present invention said basic extractant has a basicity corresponding to a pKa lower than 6.

In a further preferred embodiment of the invention, both the extraction of the free acid from the broth and the salt-splitting of the lactate salt left in the solution are conducted by LLE with a basic extractant. It is further preferred to use an extractant comprising a water-immiscible basic amine for both, and even more preferred to use extractants comprising the same amine, so that he same extractant could be used, as is or after some adjustment, in both extractions.

In yet a further preferred embodiment of the invention, the process comprises the steps of: (a) extracting most of the free lactic acid from a fermentation liquor comprising the free acid and a lactate salt by an extractant recycled from a previous step; (b) stripping the lactic acid loaded extractant obtained, preferably by back-extraction with water, at a temperature higher than that of the extraction, to form purified lactic acid solution and a stripped extractant; and (c) using the stripped extractant to recover lactic acid from the lactate salt-containing, lactic acid-depleted aqueous solution formed in step (a). The lactic acid-containing extractant formed in step (c) is suitable for extraction of free lactic acid from additional fermentation liquor, according to step (a).

The advantages of the process of the preferred embodiment of the invention include the following: (1) recovery of lactate values from the free acid fraction and salt-splitting are effected by LLE, which ensures high recovery yields, high purity, and relatively high product concentrations; (2) there is no need to operate two separate extraction cycles; (3) the stripped extractant, which has the strongest extraction power, is utilized where the strong extraction power is mostly needed, i.e., for the salt-splitting; (4) the surprising finding that even a partially loaded extractant is capable of efficient extraction of the free lactic acid in the presence of lactate salt is best utilized; and (5) an extract containing lactic acid from both the free lactic acid and the salt-splitting is fed to the stripping operation in an overall high concentration, so that the concentration of the back-extract is high. Such high concentrations of back-extract are not attainable by operating the salt-splitting separately and stripping at the same conditions. Neither can they be obtained by operating the salt-splitting and the recovery of the free acid in two separate cycles and mixing the extract for back-extraction, nor by back-extracting them separately and mixing the back-extracts.

The preferred amines for the extractant are chosen from the group consisting of primary, secondary and tertiary amines, with a total number of at least 18 carbon atoms. Mostly preferred are tertiary amines. A diluent is usually used to achieve the required physical properties.

The basicity of the extractant is easily adjusted by adding a polar solvent to the extractant. Such polar solvents enhance the extraction efficiency of the amine, which is the main active component, and are usually referred to as "enhancers." Alkanols provide very efficient enhancers. The basicity of the extractant is thus adjusted by the amount of enhancer therein, or, more precisely, by the enhancer to amine molar ratio.

The basicity of water-soluble bases is easily determined by their degree of dissociation in aqueous solution. The basicity of water-immiscible extractants is determined indirectly, through their interaction with solutes in an aqueous solution. Thus, the apparent basicity of highly basic extractants can be compared by contacting them with aqueous solutions of NaCl and determining the pH of the aqueous solution in equilibrium. The higher the pH is, the stronger is the apparent basicity of the extractant. For comparing extractants of medium or weak basicity, equilibration with acid solutions is preferred. Unlike water-soluble bases, the apparent basicity found for water-immiscible extractants is determined, in addition to the properties of the amine, by the acid in the aqueous solution, by steric hindrance to extraction, and by the diluents of the amine.

While improving the extraction, the presence of an enhancer interferes in the back-extraction. The proportion of the enhancer in the solution should therefore be adjusted, to provide for high yields in the extraction and efficient back-extraction, resulting in lactic acid solutions of high concentration. It is also possible to remove at least a part of the enhancer prior to back-extraction.

As explained hereinabove, the basicity of the extractant used in the salt-splitting should be quite high. Extraction of the free acid, on the other hand, can be conducted with a weaker extractant. A process combining salt-splitting with the recovery of the free acid could be operated in several ways, including the following:

1. Two separate extraction and back-extraction cycles can be operated.
2. Two extractions can be operated; the extracts are combined; at least part of the enhancer is removed; the resulting organic phase is back-extracted; the stripped organic phase is split into two streams; the enhancer content of each stream is adjusted to the required level, and each stream is used again in the separate extraction.
3. The extraction may be operated according to the above-described preferred process, where the stripped extractant is used first in the salt-splitting conducted on the lactic acid-depleted solution, and then for the extraction of the free lactic acid of a fresh solution.

It would have been expected that adjustment of the extractant composition would be needed in process 3 above, e.g., by adding enhancer to the extractant after stripping and prior to the salt-splitting operation, and removing some enhancer prior to the extraction of the free lactic acid. It was surprisingly found that such an adjustment is not necessary.

In preferred embodiments of the present invention, the stripped extractant formed in step (c) of the process is used as is, or after some adjustment, as the extractant in step (d), and the lactic acid-containing extractant formed in step (d) is used as is, or after some adjustment, as the extractant in step (a), wherein said adjustment comprises adding or removing a polar solvent.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

Example 1

An extractant containing 48 wt % tricaprylyl amine (Henkel's Alamine 336), 30 wt % octanol and 22 wt % kerosene was prepared by mixing the components at the desired ratio. A starting aqueous solution was prepared by mixing solutions of sodium lactate and lactic acid so that their final concentrations were 2.9 and 1.5 mol/Kg respectively (lactic acid to sodium lactate molar ratio of 1:1.9).

The aqueous solution was equilibrated at ambient temperature with three successive portions of the organic phase. Each equilibration was at aqueous to organic wt ratio of 2:1. The phases were then separated and analyzed for their lactic acid content.

The results show that 83% of the lactic acid in the aqueous phase was extracted.

Example 2

An extractant containing 48 wt % tricaprylyl amine (Henkel's Alamine 336), 20 wt % octanol and 32 wt % kerosene was prepared by mixing the components at the desired ratio. A starting aqueous solution was prepared by mixing solutions of sodium lactate and lactic acid so that their final concentrations were 1.7 and 2.8 mol/Kg respectively (lactic acid to sodium lactate molar ratio of 1:0.61).

The aqueous solution was equilibrated at ambient temperature with a portion of the organic phase. The phases were then separated and analyzed for their lactic acid content. The resulting aqueous phase was equilibrated with another portion of the organic phase, separated and analyzed. These operations were repeated several times.

The equilibrium lactic acid concentrations (mol/Kg) in the successive contacts in the aqueous and organic phases, respectively, were:
1) 2.3 and 1.9;
2) 1.6 and 1.7;
3) 0.93 and 1.43;
4) 0.23 and 0.83; and
5) 0.05 and 0.28.

Example 3

The procedure of Example 2 was repeated, except that the starting composition of the aqueous phase was 1.6 mol/Kg lactic acid and 1.0 mol/Kg sodium lactate. The equilibrium lactic acid concentrations (mol/Kg) in the successive contacts in the aqueous and organic phases, respectively, were:
1) 1.1 and 1.56;
2) 0.61 and 1.3;
3) 0.29 and 0.98;
4) 0.11 and 0.53; and
5) 0.03 and 0.187.

Example 4

The procedure in Example 2 was repeated, except that the starting composition of the aqueous phase was 0.9 mol/Kg lactic acid and 0.4 mol/Kg sodium lactate. The equilibrium lactic acid concentrations (mol/Kg) in the successive contacts in the aqueous and organic phases, respectively, were:
1) 0.24 and 0.79;
2) 0.096 and 0.395; and
3) 0.028 and 0.185.

Example 5

The procedure in Example 2 was repeated, except that the starting composition of the aqueous phase was 0.71 mol/Kg lactic acid and 0.32 equ/Kg calcium lactate. The equilibrium lactic acid concentrations (mol/Kg) in the successive contacts in the aqueous and organic phases, respectively, were:
1) 0.37 and 1.16;
2) 0.14 and 0.33; and
3) 0.009 and 0.1.

The results in Examples 1 to 5 show that nearly all the free lactic acid can be extracted from solutions comprising it along with lactate salts. This is true for various starting concentrations and acid to salt molar ratios. The distribution coefficients were high.

Example 6

An aqueous solution containing 1.2 mol/Kg lactic acid and 1.5 mol/Kg sodium lactate was counter-currently extracted with an extractant composed of 48 wt % tricaprylyl amine (Henkel's Alamine 336), 30 wt % octanol and 22 wt % kerosene. The organic to aqueous phase ratio was 1:1 wt/wt. In four stages, the extraction of the free acid was nearly completed. The lactic acid concentration in the extract formed was 1.1 mol/Kg. The extract was counter-currently back-extracted with water at 140° C. The organic to aqueous ratio was 1:0.8 wt/wt. In six stages, most of the acid was back-extracted from the extractant to form an aqueous solution of 1.25 mol/Kg lactic acid.

Example 7

The experiment in Example 6 was repeated, except that the composition of the aqueous phase was 0.7 mol/Kg lactic acid and 0.32 equ/Kg calcium lactate. The organic to aqueous ratio in the extraction was 0.87:1. The loaded extractant contained 0.7 mol/Kg lactic acid. Back-extraction in conditions similar to those in Example 6 resulted in a 0.7 mol/Kg lactic acid solution.

Concentrated sulfuric acid solution was added dropwise to the aqueous solution resulting from the extraction step, in an amount equivalent to the calcium ion content. The precipitated gypsum was removed by decantation. The resulting aqueous solution was extracted with an extractant composed as above. Practically all the lactate values in the aqueous solution were extracted as lactic acid, which was then recovered from the organic phase by back-extraction.

Example 8

An aqueous starting solution containing 2.5 mol/Kg lactic acid and 2.5 mol/Kg sodium lactate was extracted with an extractant composed as in Example 1. Practically all the lactic acid was extracted. The remaining aqueous phase was concentrated to 5 mol/Kg sodium lactate and extracted by a fresh extractant of similar composition. In organic to aqueous wt/wt ratio of 7:1, under $CO_2$ pressure of 30 atmospheres, most of the lactate values were extracted as lactic acid in eight stages. The extract obtained, comprising about 0.7 mol/Kg lactic acid, was used to extract lactic acid from another portion of the starting aqueous solution containing lactic acid. At organic to aqueous ratio of 2:1 wt/wt and six stages, more than 80% of the acid was extracted. The lactic acid concentration in the obtained extract was 1.7 mol/Kg. Back-extraction at 150° C. resulted in a 14% lactic acid solution.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the recovery of lactic acid from an aqueous solution containing lactic acid and a lactate salt, said process comprising:
   (a) contacting said aqueous solution with a water-immiscible basic amine extractant to form an amine extract containing lactic acid and an aqueous raffinate solution containing a lactate salt;
   (b) separating said amine extract from said aqueous raffinate;
   (c) stripping lactic acid from said amine extract to form a solution of lactic acid and a stripped extractant;

(d) extracting said aqueous raffinate solution separated in step (b) with said stripped extractant formed in step (c) to extract lactic acid from said aqueous raffinate solution, forming a lactic acid-containing stripped extractant; and (e) after extracting lactic acid from said aqueous raffinate solution in step (d), forming a lactic acid-containing stripped extractant, using said lactic acid-containing stripped extractant formed in step (d) as said water-immiscible basic amine extractant in step (a).

2. The process of claim 1, wherein said aqueous solution has a pH of less than 5.

3. The process of claim 1, wherein most of said lactic acid in said aqueous solution is extracted by said basic amine extractant in step (a).

4. The process of claim 3, wherein at least 70% of said lactic acid in said aqueous solution is extracted by said basic amine extractant in step (a).

5. The process of claim 1, wherein said aqueous solution comprises a fermentation broth.

6. The process of claim 1, wherein said lactic acid-containing stripped extractant comprises at least 3% lactic acid.

7. The process of claim 6, wherein said lactic acid-containing stripped extractant of comprises at least 5% lactic acid.

8. The process of claim 1, wherein said aqueous solution comprises said lactic acid and said lactate salt at a total concentration of at least 5%.

9. The process of claim 1, wherein the ratio between said lactic acid and said lactate salt in said aqueous solution is between 1:9 and 5:1.

10. The process of claim 9, wherein the ratio between said lactic acid and said lactate salt in said aqueous solution is between 1:9 and 3:1.

11. The process of claim 1, wherein the ratio between said lactic acid and said lactate salt in said aqueous solution is up to 2:1.

12. The process of claim 1, wherein said aqueous solution is concentrated prior to step (a).

13. The process according to claim 1, wherein said lactate salt is selected from the group consisting of calcium lactate, sodium lactate, and ammonium lactate.

14. The process according to claim 1, wherein said basic extractant in step (a) has a basicity corresponding to pKa lower than 7.

15. The process according to claim 1, wherein said extraction of step (a) is effected under $CO_2$ pressure.

16. The process of claim 1, wherein step (d) includes the use of an acid stronger than lactic acid so as to displace lactic acid from the lactate salt.

17. The process of claim 16, wherein said stronger acid is sulfuric acid, and a sulfate salt is formed as a by-product.

18. The process of claim 1, wherein said stripped extractant obtained in step (c) is adjusted by adding or removing a polar solvent before the use of said stripped extractant in step (d).

19. The process of claim 1, wherein said lactic acid-containing stripped extractant obtained in step (d) is adjusted by adding or removing a polar solvent before the use of said lactic acid-containing stripped extractant in step (e).

20. The process of claim 12, wherein said aqueous solution is concentrated by water evaporation prior to step (a).

* * * * *